(12) United States Patent
Hart et al.

(10) Patent No.: US 8,066,673 B2
(45) Date of Patent: Nov. 29, 2011

(54) CANNULA STABILIZATION SEAL

(75) Inventors: Charles C. Hart, Summerville, SC (US); Gigi Au, Monterey Park, CA (US); Kennii Pravongviengkham, Garden Grove, CA (US); Jeremy J. Albrecht, Ladera Ranch, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 439 days.

(21) Appl. No.: 11/277,116

(22) Filed: Mar. 21, 2006

(65) Prior Publication Data

US 2007/0225650 A1    Sep. 27, 2007

(51) Int. Cl.
*A61M 5/178* (2006.01)
(52) U.S. Cl. ............... 604/164.03; 604/164.04; 604/174
(58) Field of Classification Search ............. 604/164.03, 604/164.04, 174; 606/192
See application file for complete search history.

(56) References Cited

U.S. PATENT DOCUMENTS

| | | | |
|---|---|---|---|
| 3,039,468 A | 6/1962 | Price | |
| 3,459,175 A | 8/1969 | Miller | |
| 3,970,090 A | 7/1976 | Loiacono | |
| 4,077,412 A | 3/1978 | Moossun | |
| 4,555,242 A | 11/1985 | Saudagar | |
| 4,686,985 A | 8/1987 | Lottick | |
| 4,762,130 A * | 8/1988 | Fogarty et al. | 606/159 |
| 5,002,557 A | 3/1991 | Hasson | |
| 5,147,316 A | 9/1992 | Castillenti | |
| 5,176,697 A | 1/1993 | Hasson et al. | |
| 5,226,888 A | 7/1993 | Arney | |
| 5,290,249 A | 3/1994 | Foster et al. | |
| 5,308,356 A | 5/1994 | Blackshear, Jr. et al. | |
| 5,383,856 A | 1/1995 | Bersin | |
| 5,395,333 A | 3/1995 | Brill | |
| 5,445,615 A | 8/1995 | Yoon | |
| 5,490,843 A | 2/1996 | Hildwein et al. | |
| 5,556,385 A | 9/1996 | Andersen | |
| 5,656,013 A | 8/1997 | Yoon | |
| 5,695,448 A | 12/1997 | Kimura et al. | |

(Continued)

OTHER PUBLICATIONS

European Patent Office, The International Search Report and the Written Opinion of the International Searching Authority for International Application No. PCT/US2007/064471 mailed Nov. 14, 2007.

(Continued)

*Primary Examiner* — Kevin C Sirmons
*Assistant Examiner* — Deanna K Hall
(74) *Attorney, Agent, or Firm* — John F. Heal; David G. Majdali

(57) ABSTRACT

A stabilization seal is used with existing cannulas for forming a gas-tight seal with tissue in a body wall. The stabilization seal includes a cylindrical inflatable elongate tube having a graduated wall-thickness that is thicker in a central region and thinner in a distal-end region. The tube includes a sealing cuff, having an inflation port, for sealing around a cannula. Application of inflation pressure greatly expands the distal-end region while the central region expands slightly. Another embodiment of a stabilization seal includes an inflatable thread that is used with a cannula having a helical channel on its outer surface. An inflatable tube is wound into the channel. A distal end of the tube includes a gas-tight seal and a proximal end of the tube includes an inflation port. In the uninflated condition the nested tube is flush with the channel. Inflating the tube enlarges the cannula assembly.

16 Claims, 14 Drawing Sheets

U.S. PATENT DOCUMENTS

| | | | | |
|---|---|---|---|---|
| 5,697,946 A | * | 12/1997 | Hopper et al. | 606/185 |
| 5,713,869 A | | 2/1998 | Morejon | |
| 5,735,816 A | | 4/1998 | Lieber et al. | |
| 5,741,235 A | | 4/1998 | Knight | |
| 5,782,813 A | | 7/1998 | Yoon | |
| 5,836,913 A | | 11/1998 | Orth et al. | |
| 5,911,714 A | | 6/1999 | Wenstrom, Jr. | |
| 5,944,691 A | | 8/1999 | Querns et al. | |
| 6,030,362 A | | 2/2000 | Boussignac et al. | |
| 6,059,816 A | | 5/2000 | Moenning | |
| 6,432,085 B1 | | 8/2002 | Stellon et al. | |
| 6,451,041 B1 | | 9/2002 | Moenning et al. | |
| 6,520,933 B1 | | 2/2003 | Evans et al. | |
| 6,524,283 B1 | | 2/2003 | Hopper et al. | |
| 6,527,739 B1 | | 3/2003 | Bigus et al. | |
| 6,533,761 B2 | | 3/2003 | Bertoch et al. | |
| 6,679,860 B2 | | 1/2004 | Stiger | |
| 6,808,492 B2 | | 10/2004 | Snyder | |
| 6,887,194 B2 | | 5/2005 | Hart et al. | |
| 6,908,454 B2 | | 6/2005 | McFarlane | |
| 7,226,462 B2 | * | 6/2007 | Tanaka et al. | 606/190 |
| 2002/0100485 A1 | | 8/2002 | Stevens et al. | |
| 2003/0139758 A1 | | 7/2003 | Hopper et al. | |
| 2003/0153875 A1 | | 8/2003 | Ostfeld et al. | |
| 2004/0111061 A1 | | 6/2004 | Curran | |
| 2004/0116894 A1 | | 6/2004 | DeLegge | |
| 2004/0243167 A1 | | 12/2004 | Tanaka et al. | |
| 2005/0107665 A1 | | 5/2005 | Nady | |
| 2005/0165432 A1 | * | 7/2005 | Heinrich | 606/167 |

OTHER PUBLICATIONS

The International Bureau of WIPO, International Preliminary Report on Patentability, for International Application No. PCT/US2007/064471, dated Sep. 23, 2008.

* cited by examiner

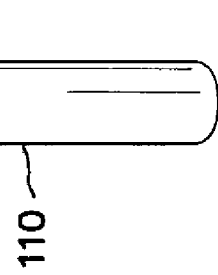
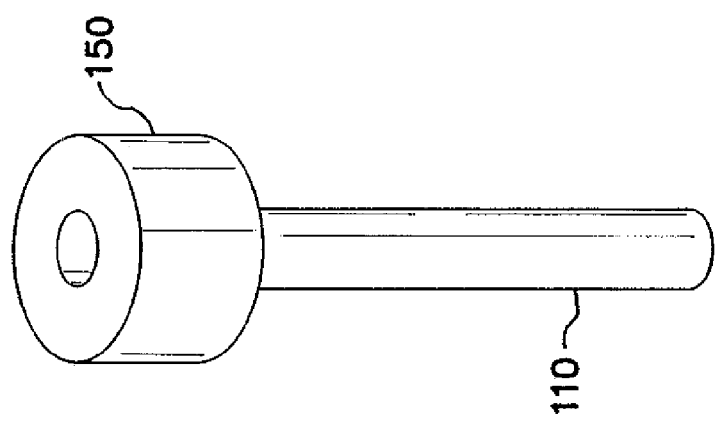
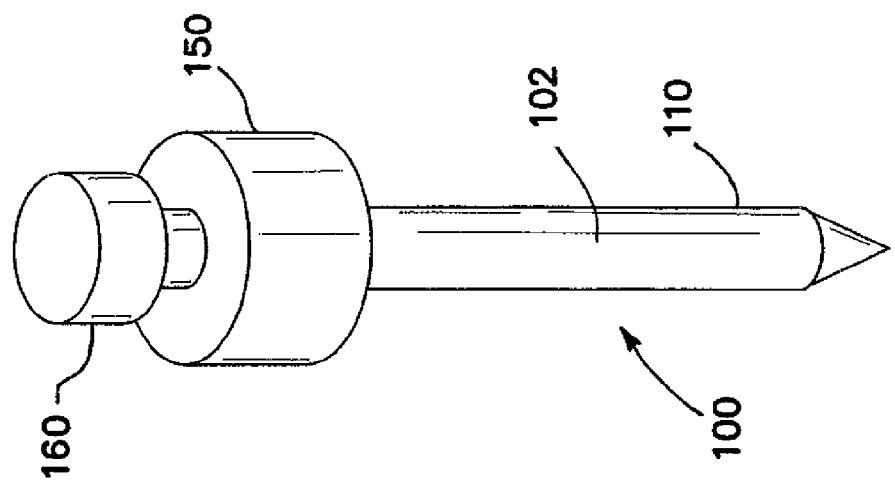

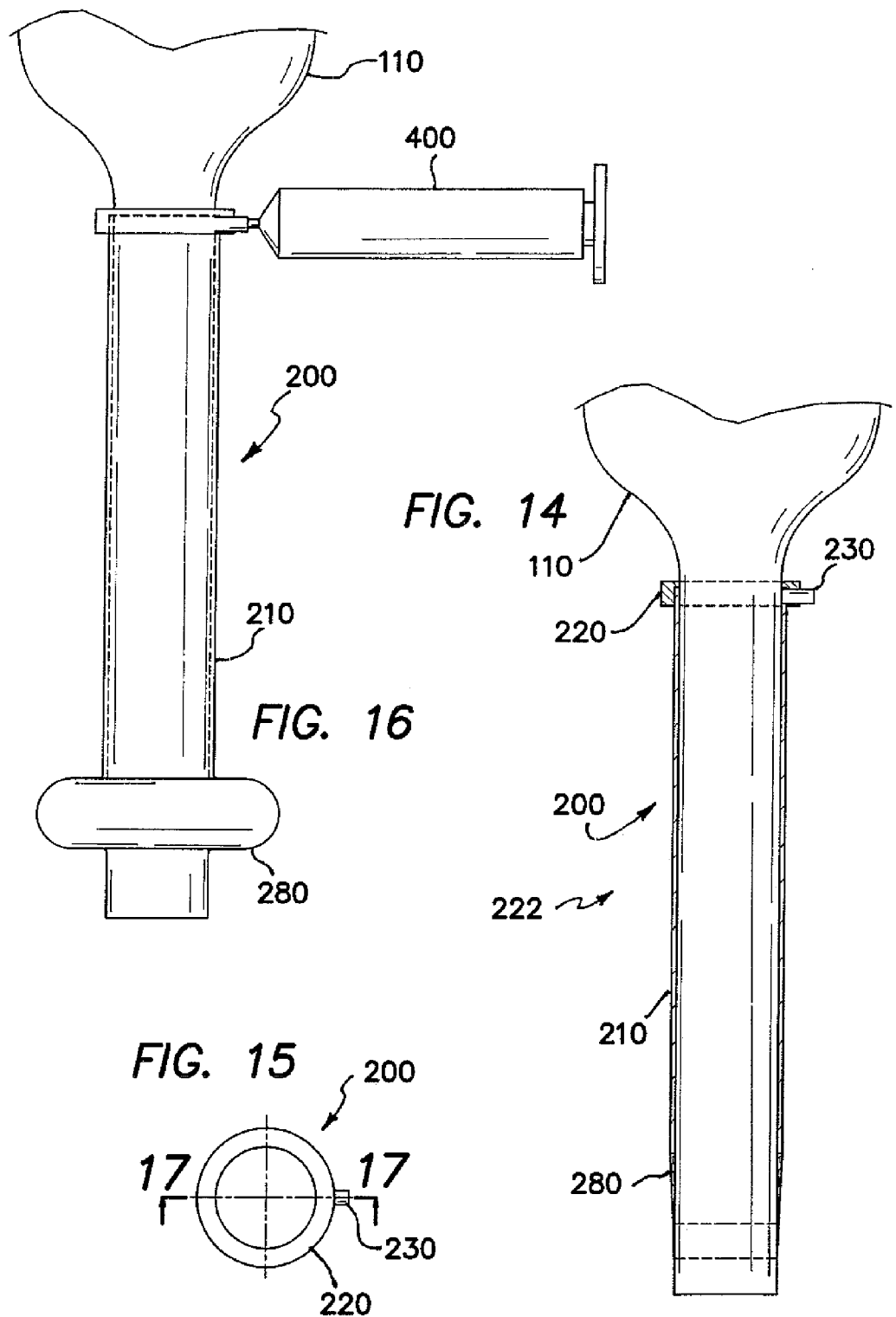

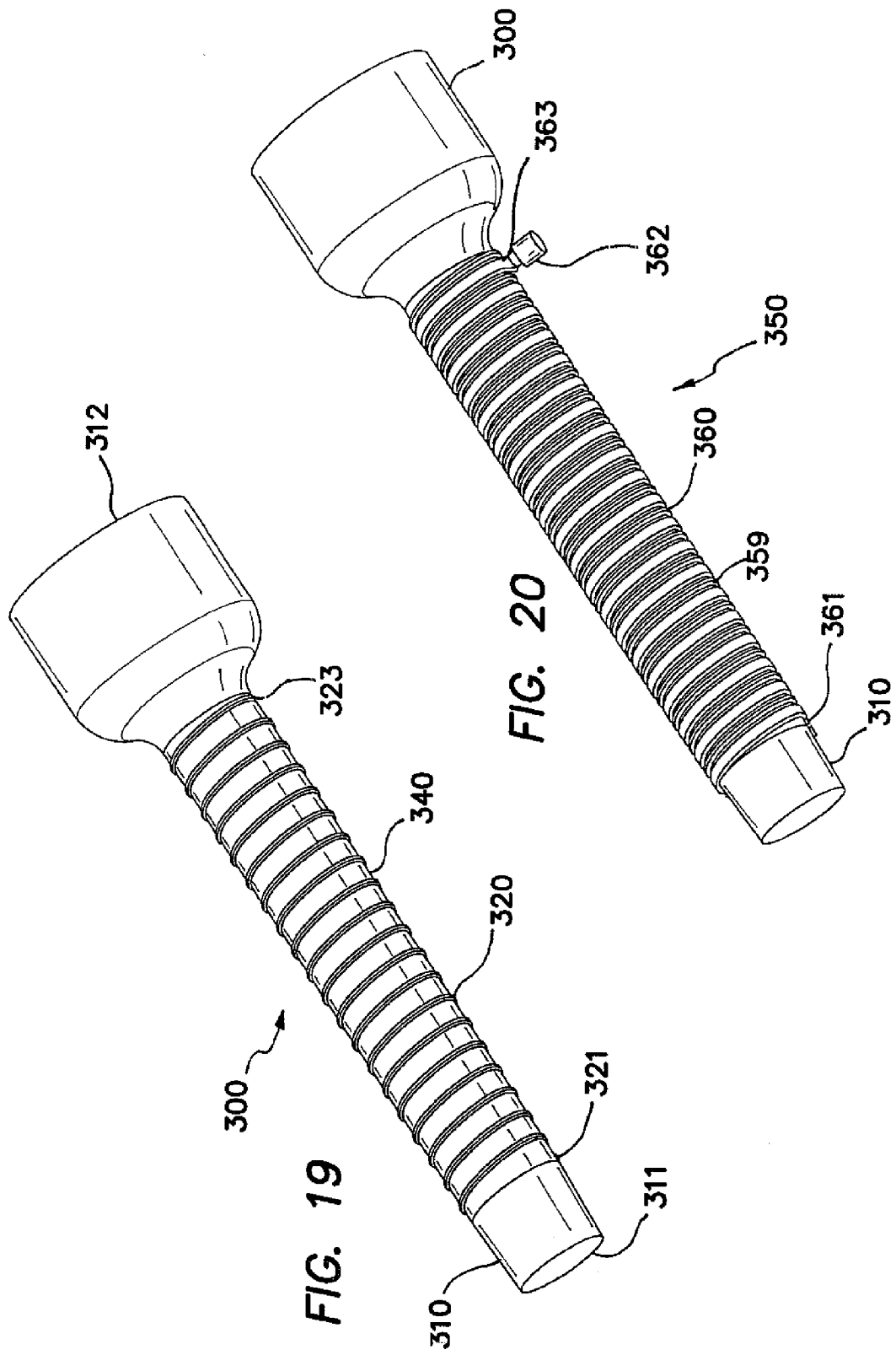

CANNULA STABILIZATION SEAL

BACKGROUND

This invention relates generally to trocar systems including cannulas and, more specifically, to trocars having a cannula stabilization seal.

Trocar systems have been of particular advantage in facilitating less invasive surgery across a body wall and within a body cavity. This is particularly true in abdominal surgery where trocars have provided a working channel across the abdominal wall to facilitate the use of instruments within the abdominal cavity.

Trocar systems typically include a cannula, which provides the working channel, and an obturator that is used to place the cannula across a body wall, such as the abdominal wall. The obturator is inserted into the working channel of the cannula and pushed through the body wall with a penetration force of sufficient magnitude to result in penetration of the body wall. Once the cannula has traversed the body wall, the obturator can be removed.

With the cannula in place in the body wall, various instruments may be inserted through the cannula into the body cavity. One or more cannulas may be used during a procedure. During the procedure, the surgeon manipulates the instruments in the cannulas, sometimes using more than one instrument at a time. The manipulation of an instrument by a surgeon may cause frictional forces between the instrument and the cannula in which the instrument is inserted. These frictional forces may result in movement of the cannula in an inward or outward direction within the body wall. If the cannula is not fixed in place, there is a potential that proximal or distal motions of the instruments through the cannula may cause the cannula to slip out of the body wall or to protrude further into the body cavity, possibly leading to injury to the patient.

The surfaces of the cannula associated with a trocar are generally smooth. The smoothness of a cannula surface makes placement of the cannula through a body wall relatively easy and safe. However, a smooth cannula may not have desired retention characteristics once the cannula has been placed through a body wall. This may present problems as instruments and specimens are removed from a body cavity through the cannula and the associated seal systems of the trocar. It is highly desirable for a cannula to remain fixed in the most appropriate position once placed.

Many solutions to the issue of trocar-cannula fixation or stabilization have been formed. These include an inflatable balloon attached to the distal portion of a cannula, raised threads or rings associated with the outer surface of the cannula, mechanically deployable enlarging portions arranged at the distal end of a cannula and suture loops or hooks associated with the proximal end of the trocar. These solutions have provided some degree of fixation or stabilization. However, there remains a need for a fixation or stabilization device that may be used with a variety of trocar-cannulas and addresses the additional requirements associated with developing laparoscopic surgical procedures and techniques. More particularly, the cannula must provide retention means to prevent the cannula from slipping out of the body cavity and provide sufficient sealing force to provide a gas-tight seal against adjacent tissue in the body wall.

SUMMARY OF THE INVENTION

This invention relates generally to access devices for providing access through a body wall and, more specifically, to the control, stabilization, fixation and sealing of such access devices. An object of the invention is to provide a cannula stabilizing and sealing system that may be used in conjunction with a wide variety of cannulas and access ports. In one embodiment, the invention includes a stabilization seal for placement on the outer surface of a surgical cannula for preventing the cannula from slipping out of a body cavity during use and to provide a substantially gas-tight seal between the cannula and adjacent tissue in the body wall. The stabilization seal includes an inflatable elongate tube having a proximal end, a distal end, a first, inner surface and a second outer surface, with the elongate tube having a substantially cylindrical shape. The stabilization seal also includes a sealing cuff at the proximal end of the elongate tube for sealing the proximal end of the tube to the cannula. The sealing cuff includes a substantially annular shape. A central region of the elongate tube includes a first thickness and a distal-end region of the elongate tube includes a second thickness that is thinner than the first thickness of the central region. The distal-end region of the elongate tube is inflatable. In one aspect, the sealing cuff includes a substantially annular seal portion. In another aspect, the seal portion includes an o-ring having an inner diameter smaller than the inner diameter of the central region of the elongate tube and adapted to form a seal with the outer surface of the cannula. In another aspect, the seal portion includes a substantially circumferential flange that is integrally formed into the seal portion with the inner diameter of the flange being smaller than the inner diameter of the central region of the elongate tube and adapted to form a seal with the outer surface of the cannula. In another aspect, the stabilization seal also includes an inflation port that is formed integrally with the sealing cuff. In another aspect, a check valve is positioned within the inflation port. In another aspect, the central region is formed to expand to a first expanded profile as inflation pressure is applied, and the distal-end region is formed to expand to a second expanded profile as inflation pressure is applied. The second expanded profile of the distal-end region is larger than the first expanded profile of the central region. In another aspect, inflation pressure applied to the stabilization seal expands the distal-end region into a substantially toroid shape. In another aspect, the central region is more rigid than the distal-end region and is substantially non-inflatable. In another aspect, the stabilization seal also includes means for coupling the distal end of the elongate tube to the distal-end region of the cannula.

In another embodiment of the invention, a cannula assembly includes a cannula and a stabilization seal. The cannula includes a substantially longitudinal tube with a proximal end, a distal end, a lumen extending between the proximal end and the distal end, a proximal-end region, a distal-end region, and a continuous helical channel on the outer surface of the cannula. The helical channel is formed by ridges on the outer surface of the cannula and extends from the proximal-end region to the distal-end region of the cannula. The stabilization seal includes an inflatable tube having a proximal end that terminates with an inflation port and a distal end that terminates in a substantially gas-tight seal. The inflatable tube is wound between the ridges that form the helical channel from the distal-end region of the cannula to the proximal-end region of the cannula such that the inflatable tube is nested between the ridges. A distal-end portion of the inflatable tube is coupled to the distal-end region of the cannula and a proximal-end portion of the inflatable tube is coupled to the proximal-end region of the cannula. In one aspect, the inflatable tube is elastomeric. In another aspect, the inflatable tube is not elastomeric. In another aspect, the distal-end portion of the inflatable tube is coupled to the distal-end region by bonding.

In another aspect the proximal-end portion of the inflatable tube is coupled to the proximal-end region of the cannula by bonding. In another aspect, the inflation port is sized and configured to allow inflation of the inflatable tube with one of a gas, air and fluid. In another aspect, the inflatable tube is generally flush with the ridges that form the helical channel on the outer surface of the cannula when the inflatable tube is in an uninflated condition. In another aspect, the inflatable tube is in a longitudinally stretched condition within the helical channel of the cannula.

DESCRIPTION OF THE DRAWINGS

FIG. 3 is a perspective view of a prior art assembled trocar and obturator;

FIG. 4 is a perspective view of a prior art assembled trocar without an obturator;

FIG. 5 is a perspective view of a prior art cannula;

FIG. 14 is a side view, partially in cross-section, depicting a cannula stabilization seal;

FIG. 15 is a plan view of a cannula stabilization seal;

FIG. 16 is a side view of a cannula stabilization seal;

FIG. 19 is a perspective view of a trocar-cannula having a helical channel;

FIG. 20 is a perspective view of a trocar-cannula having a helical track fitted with an expandable member in an un-inflated condition;

DESCRIPTION

Figure 1:
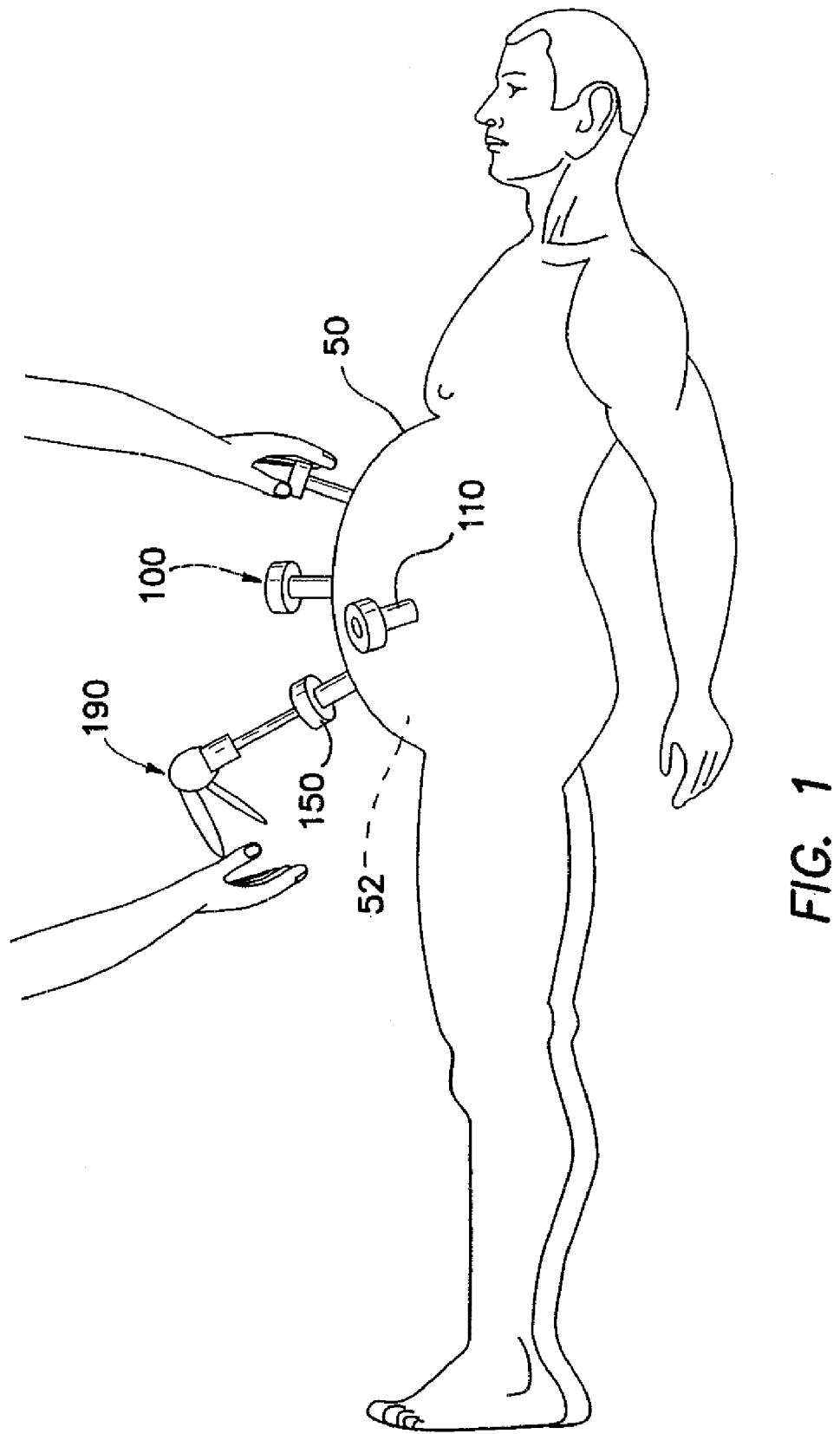
FIG. 1 is a side view of a laparoscopic surgical procedure.
Figure 2:
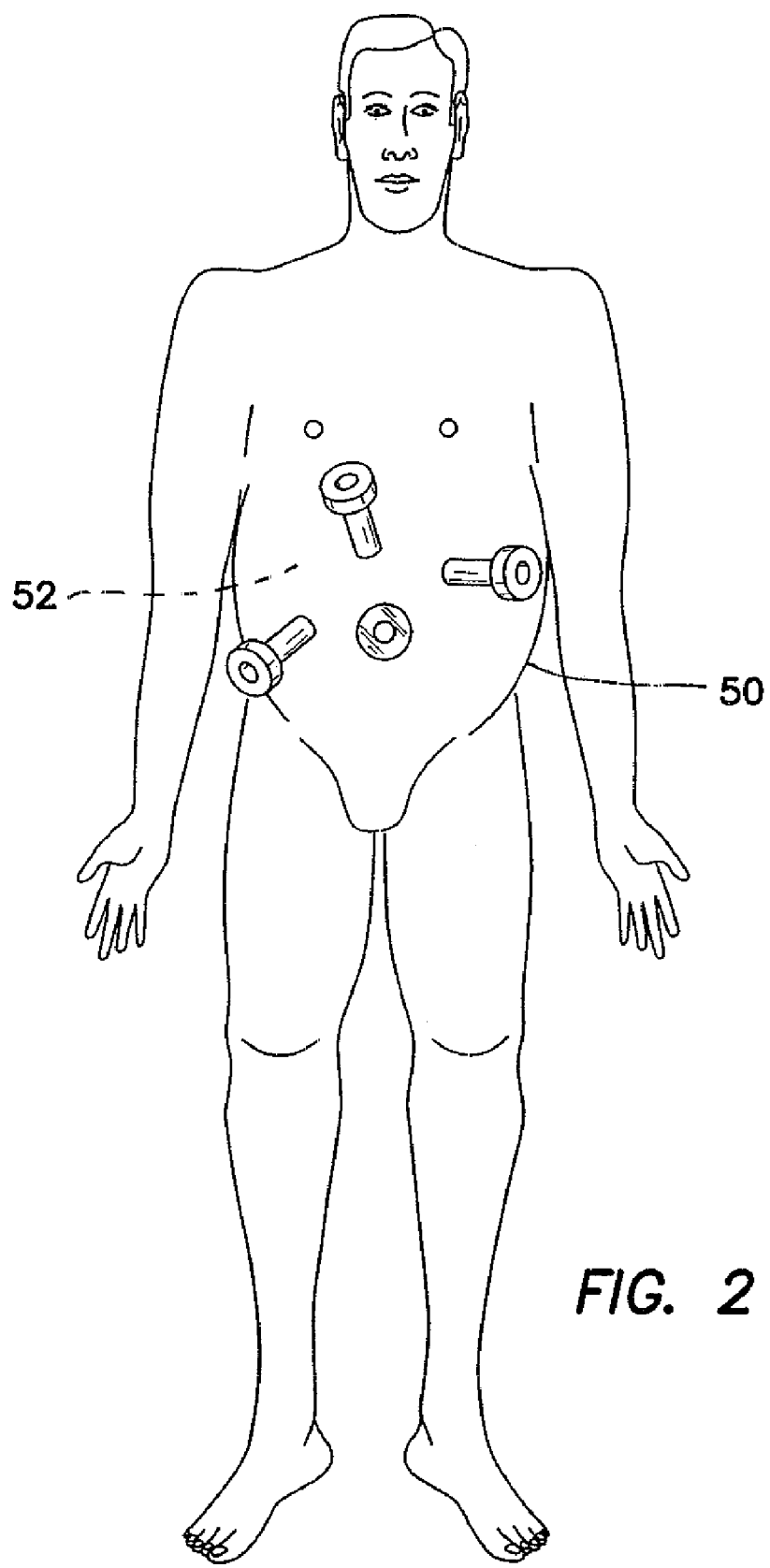
FIG. 2 is a top view of a laparoscopic surgical procedure showing placement of trocars.

With reference to FIGS. 1 and 2, a typical laparoscopic procedure is illustrated where a plurality of trocars 100 are placed through a body wall 50, such as an abdominal wall, and into a body cavity 52, such as an abdominal cavity. The body cavity 52 is insufflated, or inflated with gas, to distend the body wall 50 and provide a working space for the laparoscopic procedure. The trocars 100 each include a cannula 110 and a seal 150. Positive pressure is maintained within the body cavity 52 by the seal 150 associated with the cannula 110. In addition, the cannula 110 must fit tightly through the incision through the body wall 52 and maintain a gas-tight seal against adjacent tissue. If positive pressure is lost, either through the seal 150 associated with the cannula 110 or the seal between the cannula and the adjacent tissue, the procedure may be compromised.

As the body cavity 52 is inflated, the body wall 50 may be greatly distended. The access sites may tend to enlarge under the distention of the body wall 50 and compromise the positioning and sealing of the cannula 110. As stated above, the manipulation of instruments 190 used through the trocars 100 may result in movement of the cannulas 110 in either a proximal or distal direction and/or rotation of the cannulas 110 within the access site through the body wall 50. As this occurs, some liquefaction may take place and the preferred relationship between the cannula 110 and the body tissue may be compromised.

Referring now to FIGS. 3-5, a typical assembled trocar 100 is shown having a cannula 110, a seal housing 150 and an obturator 160. The cannula 110 typically has a smooth exterior surface 102 so that it may be inserted through the body wall 50 easily. The seal housing 150 contains a seal system that prevents retrograde gas-flow. The obturator 160 may be a cutting or piercing instrument that creates the pathway through the body wall 50 through which the cannula 110 follows. Alternatively, the obturator 160 may be a blunt-tip obturator that passes through an incision made when using the cut-down or Hassan technique to gain access to the body cavity 52. Surgical obturators 160 may be sized and configured to create a defect in tissue that is appropriate for the associated cannula 110. However, the defect may have a tendency to enlarge during a surgical procedure as the trocar 100 or cannula 110 is manipulated. As an instrument 190 is urged distally and proximally, or inserted and withdrawn, the cannula 110 may move or even be inadvertently withdrawn due to the friction between the instrument 190 and the seal 150 of the trocar housing.

Figure 8:
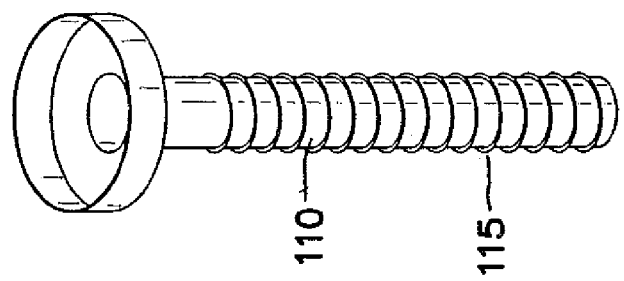
FIG. 8 is a perspective view of a prior art threaded cannula.
Figure 7:
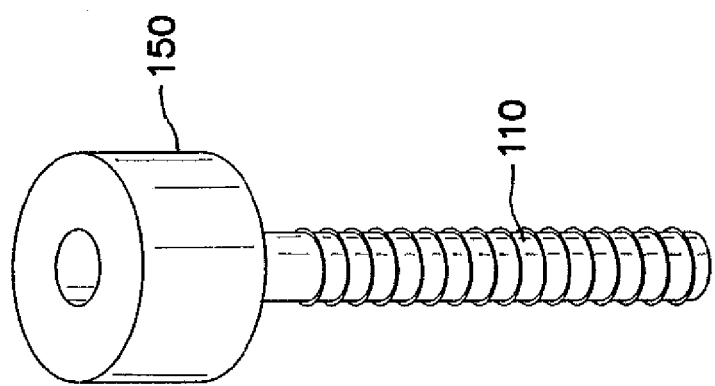
FIG. 7 is a perspective view of a prior art threaded cannula and housing.
Figure 6:
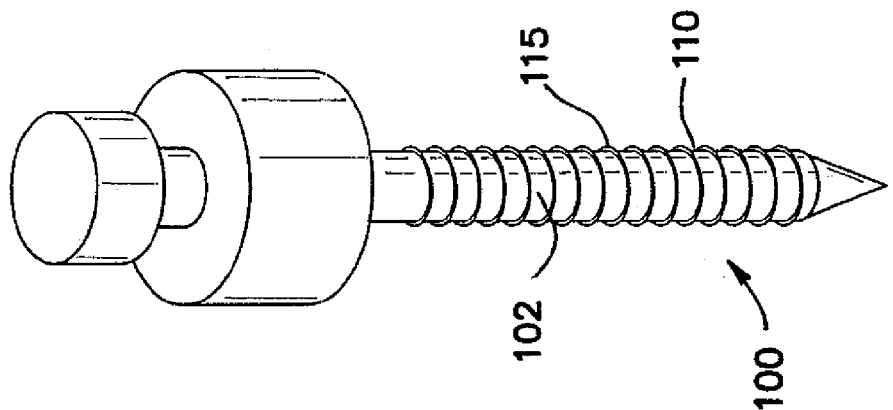
FIG. 6 is a perspective view of a prior art assembled threaded trocar and obturator.
Figures 9, 10:
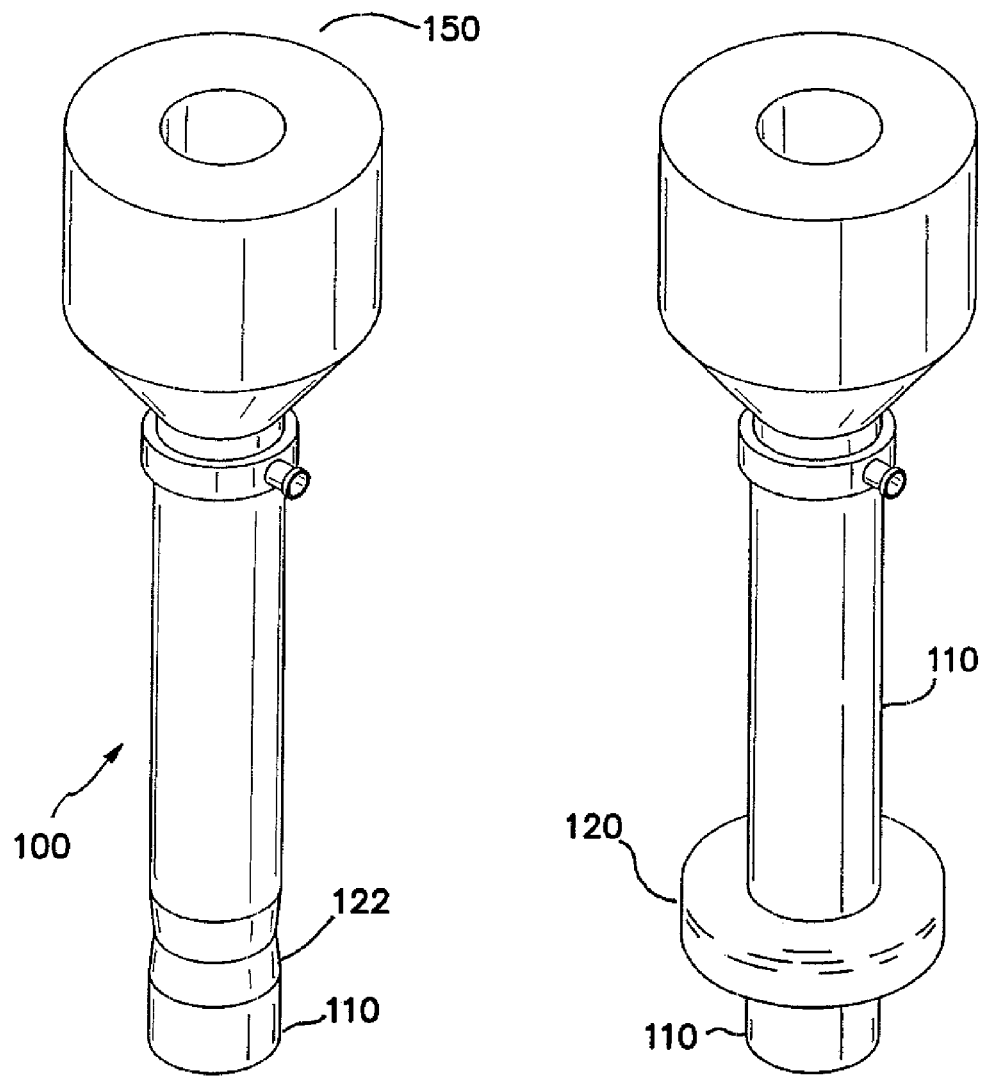
FIG. 9 is a perspective view of a prior art cannula having an uninflated balloon at the distal end.
FIG. 10 is a perspective view of a prior art cannula having an inflated balloon at the distal end.
Figure 11:
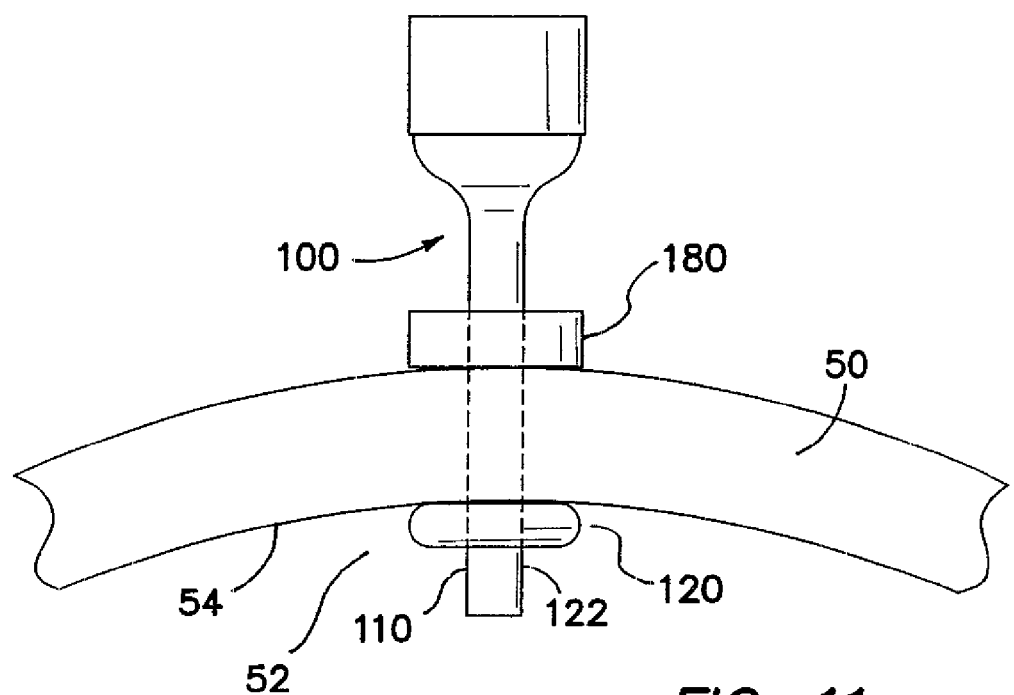
FIG. 11 illustrates a prior art trocar-cannula having a distal retention balloon placed through a body wall in a first position.
Figure 12:
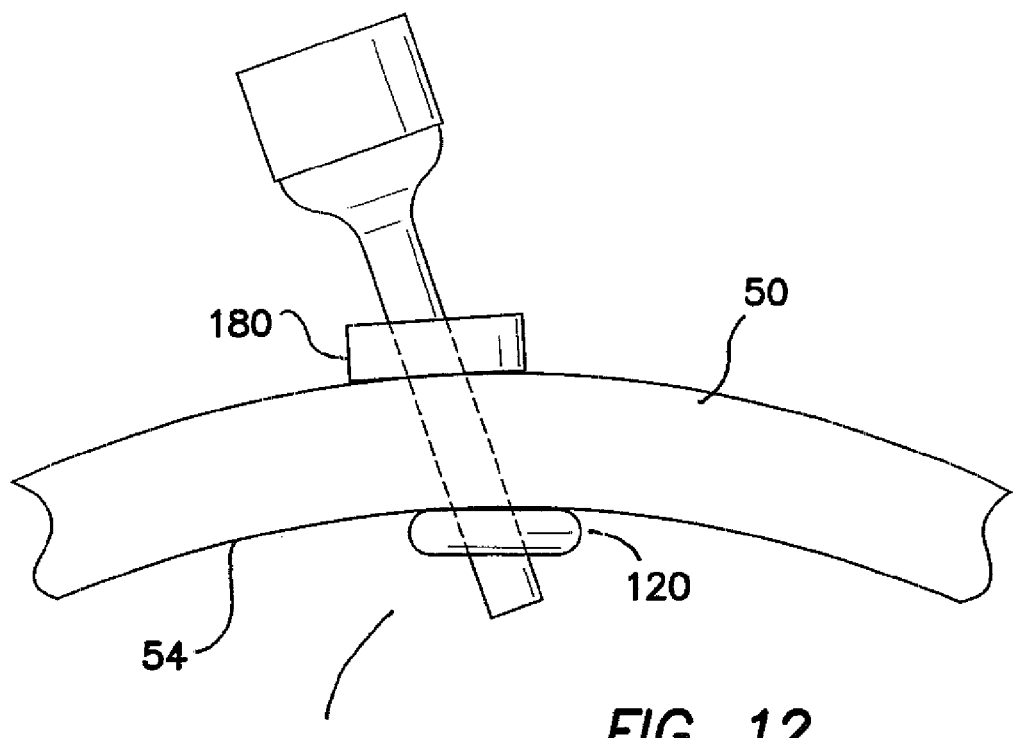
FIG. 12 illustrates a prior art trocar-cannula having a distal retention balloon placed through a body wall in a second position.
Figure 13:
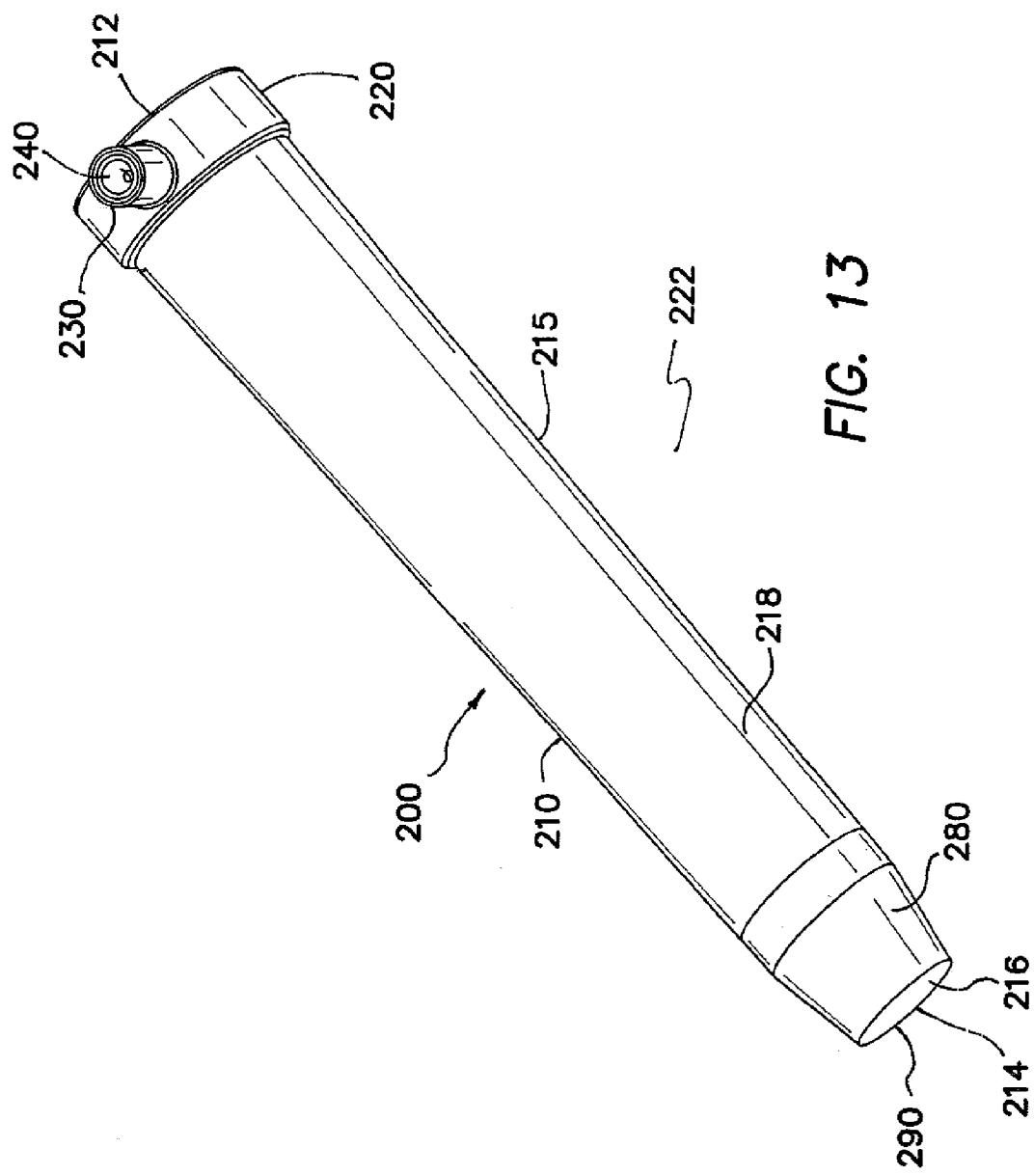
FIG. 13 is a perspective view of a cannula stabilization seal.
Figure 17:
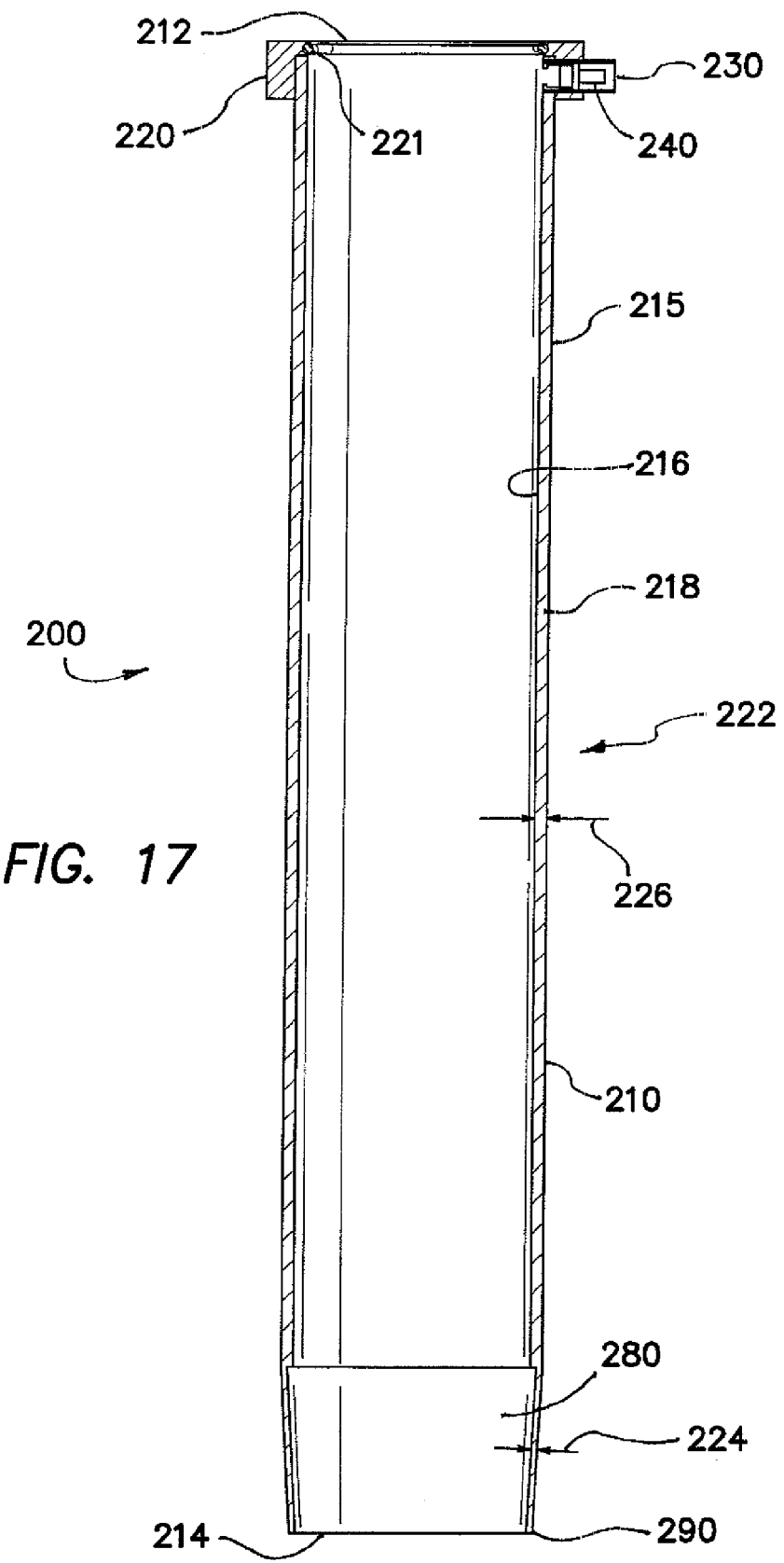
FIG. 17 is a section view of a stabilization seal taken from line 17-17 in FIG. 15.
Figure 18:
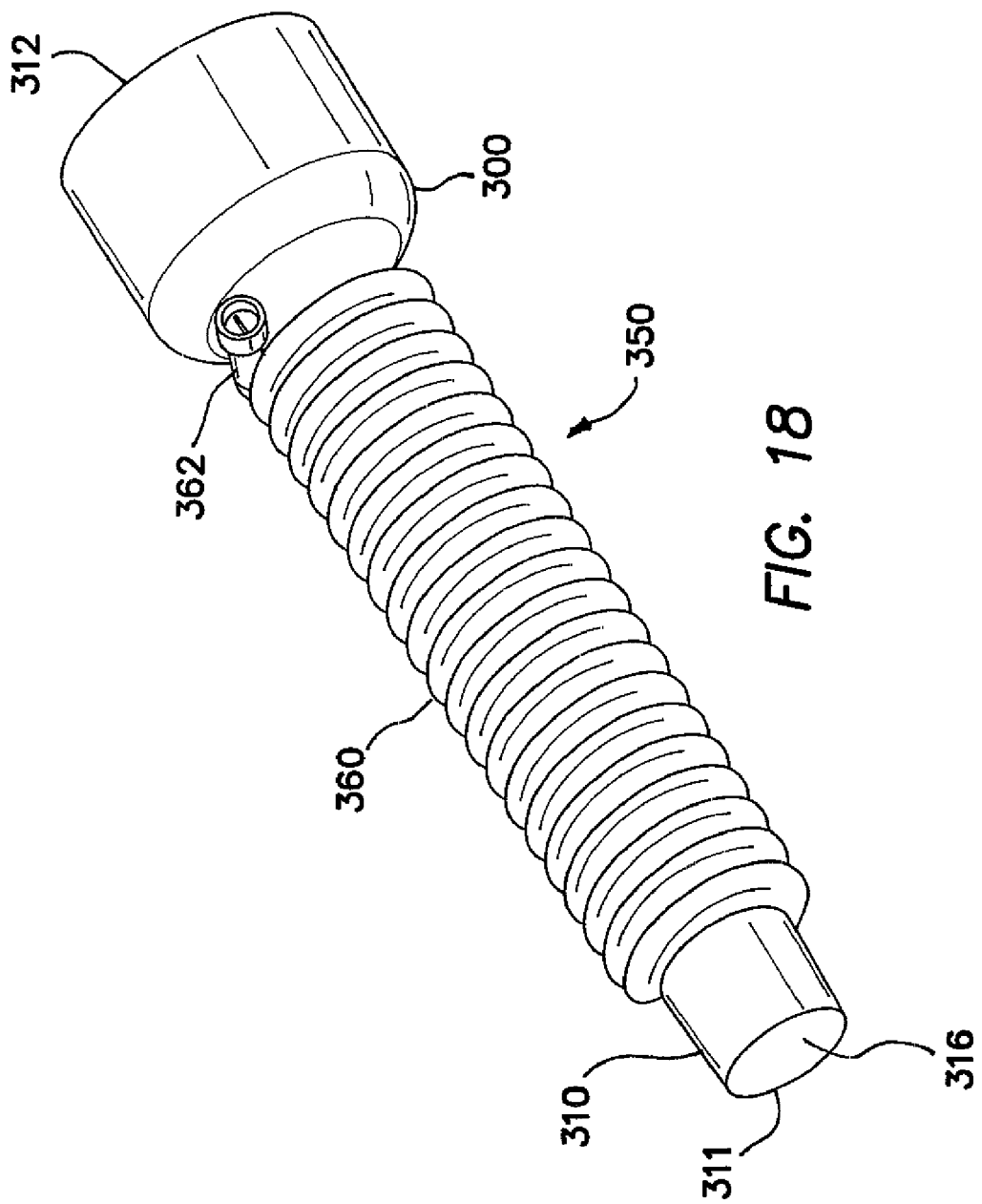
FIG. 18 is a perspective view of a trocar-cannula having an inflated helical stabilizer-seal.
Figure 21:
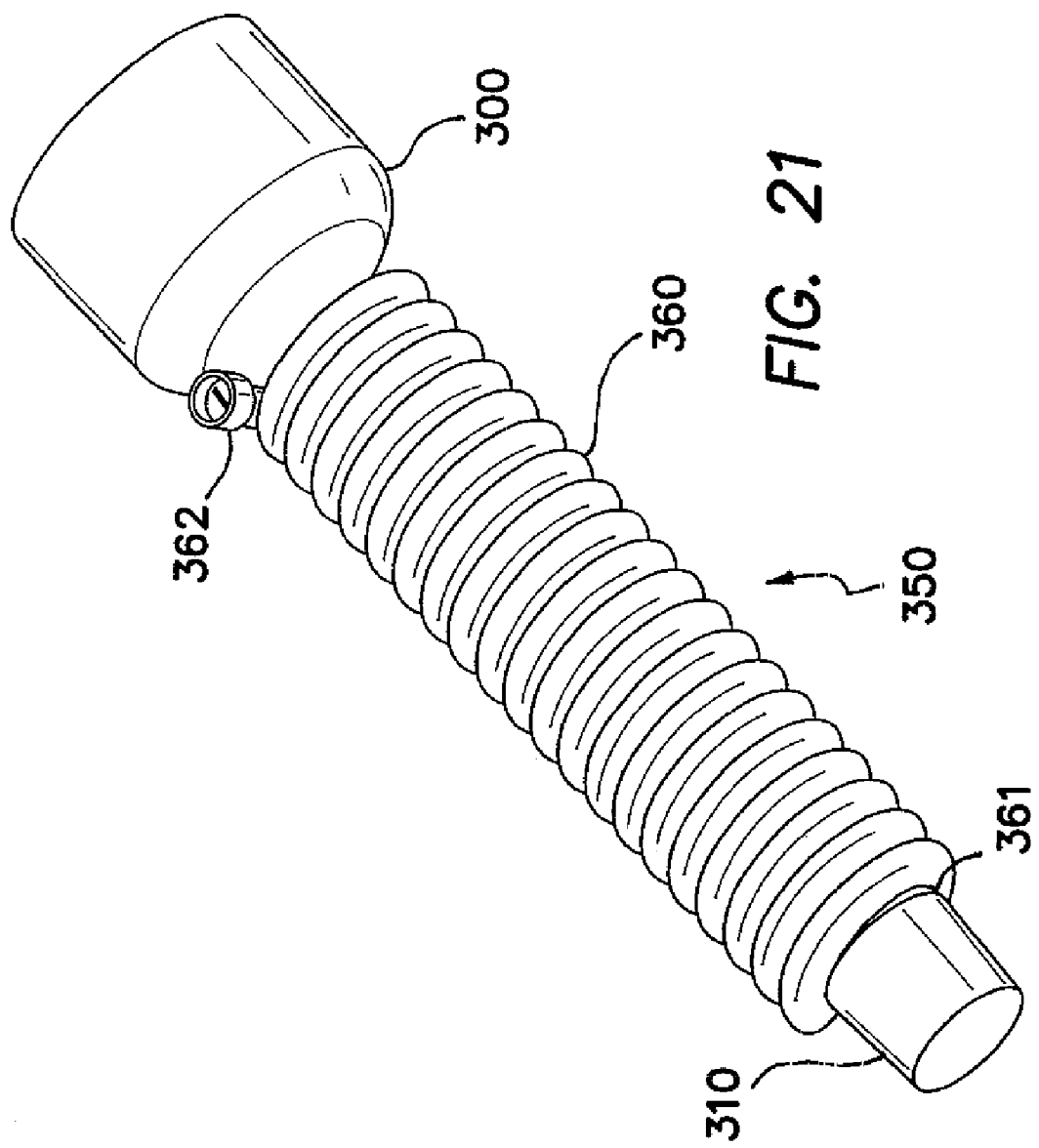
FIG. 21 is a perspective view of inflatable threads in an inflated condition on a cannula.
Figure 22:
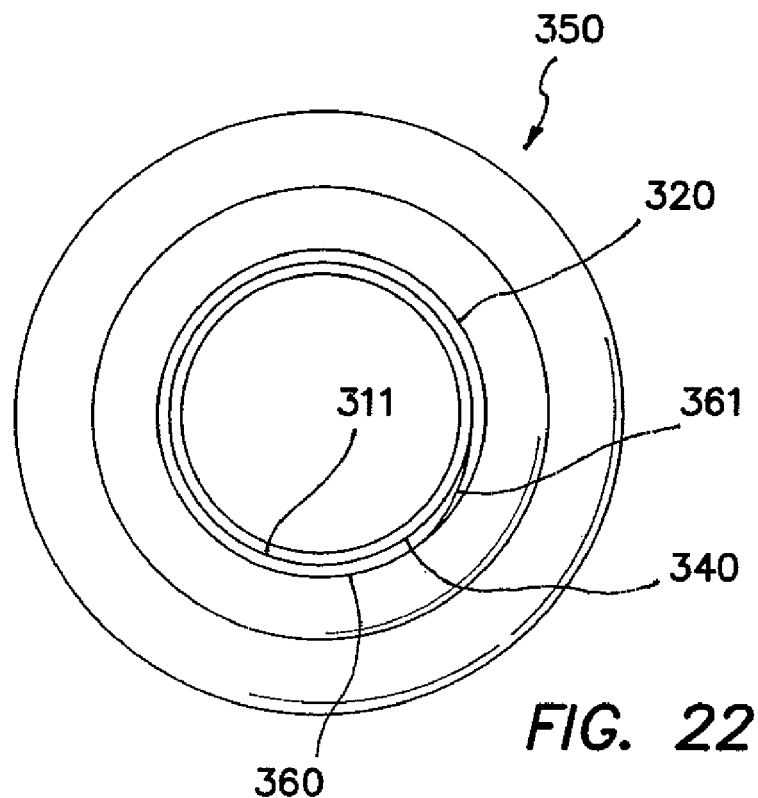
FIG. 22 is a distal end view of the un-inflated expandable member.
Figure 23:
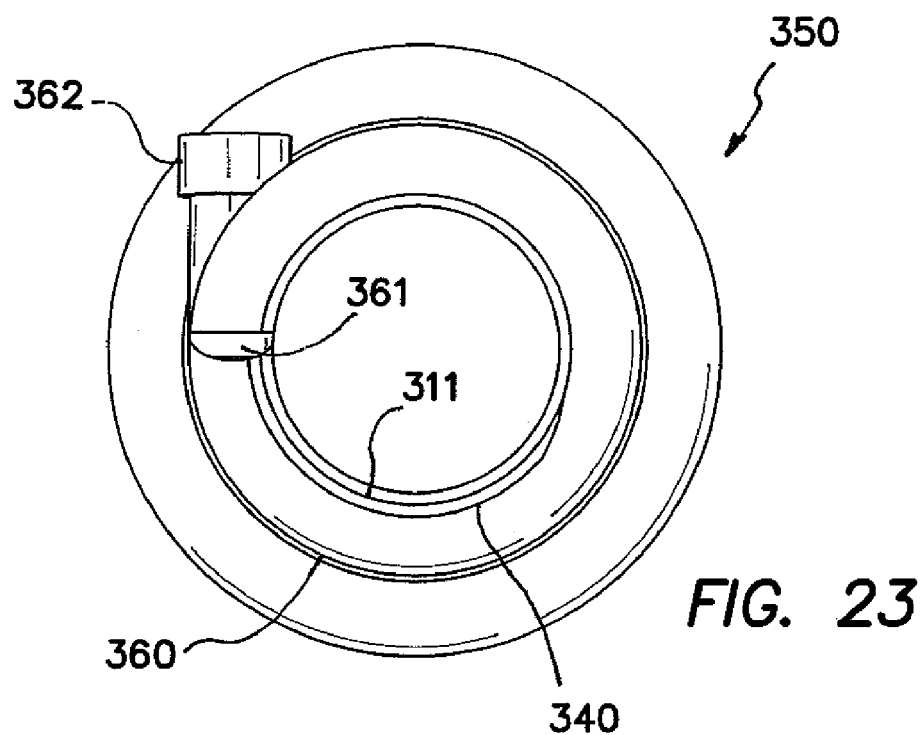
FIG. 23 is a distal end view of the inflated expandable member forming inflated threads.
Figure 26:
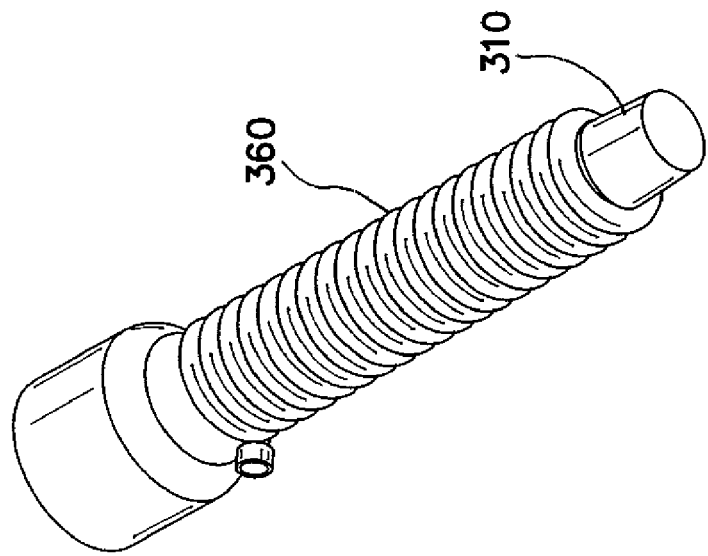
FIG. 26 is a perspective view of the expandable member in an inflated condition and in association with the cannula.
Figure 25:
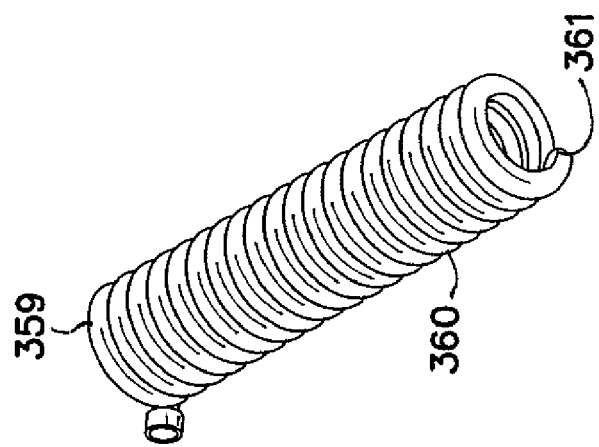
FIG. 25 is a perspective view of the expandable member in an inflated condition.
Figure 24:
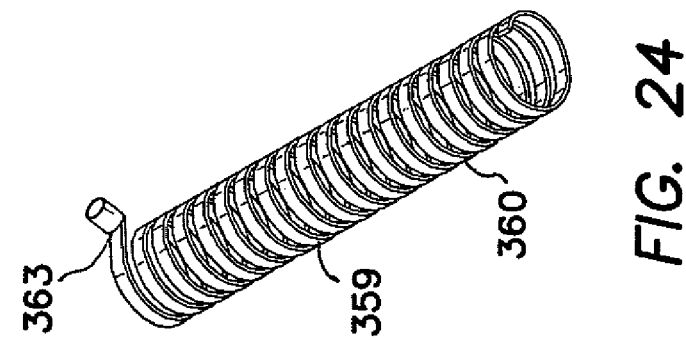
FIG. 24 is a perspective view of the expandable member in an uninflated condition.

With reference to FIGS. 6-8, a trocar 100 or access device is shown where the outer surface 102 of the cannula 110 includes a plurality of raised features 115. These raised features 115 are sized and configured to increase resistance to proximal and distal motion as instruments 190 are maneuvered and especially as specimens are removed through the trocar 100. The prior art includes either sequential raised rings or a raised coarse-thread 115. While the rings or threads 115 of the prior art may stabilize the cannula 110 to some degree, they do not necessarily seal the cannula 110 against the adjacent tissue of a body wall 50. There may be gas loss associated with the use of these systems. The raised rings or threads 115 also increase the insertion force required to penetrate a body wall 50. The insertion force may be reduced in the instance of a continuous coarse thread 115 in comparison to a sequence of discrete raised rings or features as a threaded cannula 110 may actually be "screwed" into the tissue defect in accordance with the thread direction and pitch, rather than pushed through without appropriate rotation.

With reference to FIGS. 9-12, a surgical access device 100 according to prior art includes a cannula 110 having an inflatable balloon 120 associated with the distal-end portion 120 of the cannula. The balloon 120 is sized and configured to fit snugly around the cannula 110 in the uninflated condition. The balloon 120 is inflated after the cannula 110 is properly placed through the body wall 50 and into the body cavity 52. The balloon 120 is generally held against the interior surface 54 of the body wall 50 by a counter-force that is associated with a sliding counter-force member 180. The sliding counter-force member is associated with the proximal portion of the cannula 110. The balloons 120 associated with the devices of the prior art are typically "thick-walled" structures constructed as part of the cannula 110. The balloon 120 is generally bonded to the distal-end portion 122 of the cannula 110 and an inflation channel or lumen is provided within the wall of the cannula 110. This construction can be complicated and expensive. Additionally, this construction requires that the cannula 110 and associated balloon 120 be inserted whether or not the balloon is required or used.

Referring to FIGS. 13-17, one embodiment of the stabilization seal 200 of the present invention includes a substantially cylindrical inflatable elongate tube 210 having a proximal end 212, a distal end 214, a first, inner surface 216, a second, outer surface 218 and a graduated wall-thickness. The proximal end 212 of the elongate body 210 includes a substantially annular sealing cuff 220 or enlargement that is sized and configured to seal around an associated cannula 110 in a gas-tight arrangement. A portion of the "sealing-cuff" 220 may include an integrally formed, substantially annular, elastomeric seal portion 221 resembling an o-ring or flange that exhibits strong "hoop-force" upon the cannula 110. The inner diameter of the o-ring or flange may be smaller than the inner diameter of the central region of the elongate tube and adapted to form a seal with the outer surface of the cannula. The sealing-cuff 220 may be formed having an inflation port 230 through which positive gas-pressure may be applied or withdrawn. A central region 222 of the inflatable elongate body 210 may be formed to expand slightly as inflation pressure is applied. A distal-end region 280 of the elongate body 210 includes a region where the wall-thickness 224 is greatly reduced from the wall thickness 226 of the central portion 222. The reduced wall-thickness 224 of the distal-end region 280 of the elongate body 210 allows gas pressure to greatly expand the distal end portion 280 to form a retention feature or toroid-shaped balloon 120. (See FIG. 16) The combination of a retention balloon 120 and a slightly enlargeable central portion 222 provides retention at the distal end 214 of the elongate body 210 and a gas-tight occlusion along the elongate body. There is, therefore, no requirement for a proximal-end retention member 180 to urge the retention balloon 120 toward the inner body-wall surface 54. (See FIG. 10.) Additionally, the unitary construction of the stabilization seal 200 allows for very smooth, thin-walled sections and inexpensive processing.

The stabilization seal 200 may be manufactured as a single molded elastomeric component having a retention-cuff 220 with an integral inflation-port 230, a semi-inflatable central region 222 of the elongate body 210 and a fully inflatable distal toroid-balloon 280. Alternatively, the stabilization seal 200 may be manufactured as a single molded non-elastic, inflatable component having a retention cuff 220 with an integral inflation port 230, a semi-inflatable central region 222 of the elongate body 210 and a fully inflatable distal toroid balloon 280. Such non-elastic materials may include polyethylene, polyurethane, polyolefin or the like. These materials may be processed to form inflatable or expandable, non-distensible, components that differ from elastomeric or distensible components. The inflation-port 230 may include a one-way seal or check-valve 240 that is interruptible for inflation and deflation of the inflatable portions 222, 280.

One embodiment of the stabilization seal 200 may be used with existing trocars 100 and cannulas 110 without alteration to the cannulas. The stabilization seal 200 may be packaged separately and placed onto a cannula 110 as needed. A distinct advantage can be seen in that if a stabilization seal 200 is broken or begins to leak, it can be easily replaced. However, if the retention balloon 120 is constructed as part of the trocar 100, as in the prior art, the entire trocar 100 must be replaced if a failure of the balloon 120 occurs, potentially resulting in elevated risk and cost.

There are many materials suitable for manufacturing the stabilization seal 200, including elastomerics such as silicone rubber, polyisoprene rubber, nitrile, latex, vinyl, styrene block co-polymer, polyurethane or the like. This list is included as an example only and is in no way considered as a limitation of the materials that may be used to construct the stabilization seal 200. Those familiar in the art will recognize that other materials may be used successfully and the use of such materials is contemplated as within the scope of the present invention.

One embodiment of the stabilization seal 200 includes a rigid elongate body 210 having an elastomeric seal 220 and an inflation port 230 associated with the proximal end 212 and a thin-walled elastomeric balloon portion 280 associated with the distal end 214. The distal end 290 of the balloon portion 280 may be bonded or otherwise coupled to the distal-end region 116 of the cannula 110 or may have a strengthened distal-end sealing portion.

A further alternate embodiment of the stabilization seal 200 includes an elongate cylindrical body 210 having a proximal end 212 and a distal end 214. The proximal end 212 may comprise a reinforced cuff 220 for coupling the stabilization seal to a cannula 110. The cuff 220 may have an inflation port 230 for inflating portions of the device 200. The central body 222 and distal-end region 280 may comprise a plurality of inflatable portions 215, 280. The first inflatable region 215 may form a seal between a cannula 110 and adjacent tissue. The second inflatable region 280 may form a retention member 120 for retention of the associated cannula 110. The first and second inflatable regions 215, 280 may be formed by molding progressively thinner wall sections 224, 226 distally along the elongate body 210.

During a surgical procedure in which the stabilization seal 200 of the present invention may be used, a surgeon may gain access to the abdominal cavity 52 through the abdominal wall 50 by using the "Hassan" or "cut-down" technique. However, use of the Hassan or cut-down technique often leaves a defect larger than the trocar that will be located through the incision. Therefore, it is necessary to provide a means to seal the incision after the trocar has been inserted in order to insufflate the patient's abdominal cavity. The stabilization seal 200 of the present invention provides such sealing means.

Once an incision is made in the body wall 50 to gain entry to the body cavity 52, such as the abdominal cavity, a cannula 110 having a stabilization seal 200 coupled to it is inserted through the incision until the second inflatable region 280 of the stabilization seal is within the body cavity. A syringe 400 may be inserted into the port 230 and used to inflate the first and second inflatable regions 215, 280 by injecting gas or fluid into the port 230. With the incision sealed, the body cavity 52, such as the abdominal cavity, may be insufflated with $CO_2$ or a similar gas. To deflate the stabilization seal 200 for removal from the body cavity 52, the check valve 240 within the port 230 may be depressed to release the gas or fluid from the stabilization seal. The syringe 400 may be used to depress the check valve 240 within the port 230 and the syringe used to pull the gas or fluid from the stabilization seal, thereby deflating the stabilization seal.

With reference to FIGS. 18-26, another embodiment of a stabilization seal 350 of the present invention is depicted having an inflatable thread 360. This embodiment of the invention may be used with a trocar cannula 300 having an elongate body 310, a proximal end 312, a distal end 311, a lumen 316 extending between the proximal end 312 and the distal end 311, and a continuous, coarse, helical channel 340 formed by ridges 320 on the outer surface of the elongate body. The helical channel 340 extends from a proximal-end region 323 of the elongate body 310 to a distal-end region 321 of the elongate body. A thin-walled inflatable tube 359 is wound into the helical channel 340, such that it is nested between the ridges 320, from the distal-end region 321 of the elongate body 310 to the proximal-end region 323 of the elongate body. A distal end 361 of the tube 359 terminates in a substantially gas-tight seal. A distal-end portion of the inflatable tube 359 is coupled to the distal-end region 321 of the cannula 300, such as by bonding or other methods that are well known in the art. A proximal end 363 of the tube 359 is terminated with a fitting 362, such as an inflation port, that is sized and configured to allow inflation of the tube with gas, air or fluid. A proximal-end portion of the inflatable tube 359 is coupled to the proximal-end region 323 of the cannula 300, such as by bonding or other methods that are well known in the art. The tube 359 may be formed from silicone rubber, polyisoprene, latex, nitrile, vinyl, polyurethane, styrene block co-polymer, or other like materials that are well known in the art. This list is included as an example only and is in no way considered as a limitation of the materials that may be used to construct the stabilization seal 350. Those familiar in the art will recognize that other materials may be used successfully and the use of such materials is contemplated as within the scope of the present invention.

In the uninflated condition (see FIG. 20), the nested tube 359 is generally flush with the raised ridges 320 that form the helical channel 340 so that a substantially smooth surface is presented as the cannula 310 is inserted through a body wall 50. In addition, the inflatable tube 359 is stretched longitudinally as it is wound into the helical channel 340 so that during inflation it does not expand radially away from the cannula as the length of the inflatable tube increases under inflation pressure to form the inflated thread 360. Adjacent loops of the inflatable tube 359 are separated by the ridges 320 of the cannula when the inflatable tube is in an uninflated state. Once the cannula 310 has been placed through a body wall 50, the nested tube 359 may be inflated so that the cannula is substantially enlarged so as to fit securely within the defect in the body wall 50 through which it was inserted. Adjacent loops of the inflatable tube 359 are in contact with each other when the inflatable tube is in an inflated state. A gas-tight relationship is formed between the enlarged cannula 360 and the adjacent tissue in the body wall 50. This is especially important when the procedure for inserting the cannula 310 through a body wall 50 includes a "cut-down" technique, such as the "Hassan technique," which produces a much larger and looser fitting defect than techniques that include a simple piercing of the body wall.

The inflatable thread 360 of the stabilization seal 350 of the present invention provides improved "trocar mobility" over prior art trocars. The instruments 190 used through a trocar 100 must be able to reach areas that are not always directly in the inserted "line of sight." In other words, the trocars 100 must be positioned obliquely and held in relatively awkward positions for use and subsequently moved back and forth between one position and another. A large abutment (see FIGS. 11 and, 12), such as an inflated balloon 120 at the distal end of the cannula 110, may present a restriction to such movement and restrict "trocar mobility." The inflatable threaded portion 360 of the stabilization seal 350 of the present invention allows the cannula 310 to be positioned and subsequently repositioned more easily than a distal balloon 120 allows.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of many embodiments. Those skilled in the art will envision other modifications within the scope and spirit of the present invention as defined by the following claims.

The invention claimed is:

1. A stabilization seal for placement on the outer surface of a surgical cannula for preventing the cannula from slipping out of a body cavity during use and to provide a substantially gas-tight seal between the cannula and adjacent tissue in the body wall, the stabilization seal comprising:
    an inflatable elongate tube having a proximal end, a distal end, a first, inner surface and a second outer surface, the elongate tube having a substantially cylindrical shape such that the inner surface defines a lumen therein adapted to receive the outer surface of the surgical cannula, the lumen having an inner diameter;
    a sealing cuff at the proximal end of the elongate tube for sealing the proximal end of the tube to the cannula, the sealing cuff having a substantially annular shape and the sealing cuff having an inner diameter smaller than the inner diameter of the lumen, the inner diameter of the sealing cuff sized and configured to contact the cannula in sealing engagement;
    a central region of the elongate tube having a first thickness; and
    a distal-end region of the elongate tube having a second thickness that is thinner than the first thickness of the central region, the distal-end region of the elongate tube being inflatable to an inflated position defining a retention member, the distal-end region comprising a distal end sealing portion sized and configured to contact the cannula in sealing engagement.

2. The stabilization seal of claim 1, the sealing cuff including a substantially annular elastomeric seal portion.

3. The stabilization seal of claim 2, the elastomeric seal portion comprising an O-ring, the inner diameter of the O-ring being smaller than the inner diameter of the central region of the elongate tube and adapted to form a seal with the outer surface of the cannula.

4. The stabilization seal of claim 2, the elastomeric seal portion comprising a substantially circumferential flange integrally formed into the seal portion, the flange adapted to form a seal with the outer surface of the cannula.

5. The stabilization seal of claim 1, further comprising:
    an inflation port formed integrally with the sealing cuff.

6. The stabilization seal of claim 5, further comprising:
    a check valve positioned within the inflation port.

7. The stabilization seal of claim 1, wherein:
    the central region is formed to expand to a first expanded profile as inflation pressure is applied, and
    the distal-end region is formed to expand to a second expanded profile as inflation pressure is applied, the second expanded profile of the distal-end region being larger than the first expanded profile of the central region.

8. The stabilization seal of claim 7, wherein inflation pressure applied to the stabilization seal expands the distal-end region into a substantially toroid shape.

9. The stabilization seal of claim 1, wherein:
the central region is more rigid than the distal-end region, and
the central region is substantially non-inflatable.

10. The stabilization seal of claim 1, wherein the inflatable elongate tube comprises no proximal-end retention member.

11. The stabilization seal of claim 1, wherein the inflatable elongate tube is couplable to the cannula such that the inner surface of the inflatable elongate tube is immediately adjacent an outer wall of the cannula to define a first inflatable region from the outer wall of the cannula to the inner surface of the inflatable elongate tube at the central region of the inflatable elongate tube and a second inflatable region from the outer wall of the cannula to the inner surface of the inflatable elongate tube at the distal-end region.

12. A stabilization seal for placement on the outer surface of a surgical cannula, the stabilization seal comprising:
an inflatable elongate tube comprising:
a proximal end;
a distal end having a distal end region adjacent the distal end;
a central region extending between the proximal end and the distal end, the central region having a first thickness and the distal end region having a second thickness smaller than the first thickness;
an inner surface defining a lumen extending from the proximal end to the distal end, the lumen having an inner diameter and the lumen adapted to receive the surgical cannula therein such that the surgical cannula is immediately adjacent the inner surface of the elongate tube;
an outer surface;
a sealing cuff formed at the proximal end of the elongate tube, the sealing cuff having a substantially annular shape and the sealing cuff having an inner diameter smaller than the inner diameter of the lumen; and
a sealing portion at the distal end of the elongate tube,
wherein the central region is inflatable to an expanded position defining an occlusive surface upon application of an inflation pressure; and the distal end region of the elongate tube is inflatable to an inflated position defining a retention member.

13. The stabilization seal of claim 12, wherein the inflatable elongate tube is couplable to the surgical cannula to define an inflatable volume bounded by the outer surface of the surgical cannula, the inner surface of the lumen of the elongate tube, the sealing cuff, and the sealing portion.

14. The stabilization seal of claim 12, further comprising: an inflation port formed integrally with the sealing cuff.

15. The stabilization seal of claim 14, further comprising: a check valve positioned within the inflation port.

16. The stabilization seal of claim 12, wherein the inflatable elongate tube comprises no proximal-end retention member.

* * * * *